United States Patent
Schulhoff et al.

(10) Patent No.: US 6,309,470 B1
(45) Date of Patent: Oct. 30, 2001

(54) COMPOSITION AND METHOD FOR CLEANING SURFACES

(75) Inventors: Jeffrey Schulhoff, Oklahoma City, OK (US); Christian Schaal, Nettetal (DE)

(73) Assignee: Water Whole International, Inc., Norman, OK (US)

( * ) Notice: Subject to any disclaimer, the term of this patent is extended or adjusted under 35 U.S.C. 154(b) by 0 days.

(21) Appl. No.: 09/584,892

(22) Filed: Jun. 1, 2000

Related U.S. Application Data

(63) Continuation-in-part of application No. 09/324,383, filed on Jun. 2, 1999.

(51) Int. Cl.$^7$ .................................................... C23G 1/02
(52) U.S. Cl. ................... 134/26; 134/2; 134/3; 134/22.1; 134/22.11; 134/28; 134/36; 134/41; 134/42; 510/119; 510/245
(58) Field of Search .............................. 134/2, 3, 22.1, 134/22.11, 26, 28, 36, 41, 42; 510/119, 245

(56) References Cited

U.S. PATENT DOCUMENTS

| | | | | |
|---|---|---|---|---|
| 4,199,469 | * | 4/1980 | Walzer | 252/146 |
| 4,780,150 | * | 10/1988 | Anderson | 134/3 |
| 4,851,149 | * | 7/1989 | Carandang | 252/147 |
| 4,885,136 | * | 12/1989 | Katayama et al. | 422/15 |
| 5,280,042 | * | 1/1994 | Lopes | 514/557 |
| 6,051,108 | * | 4/2000 | O'Neal, Jr. | 162/199 |

OTHER PUBLICATIONS

Written Opinion for PCT/US00/14949, filed Jun. 01, 2000.*

* cited by examiner

*Primary Examiner*—Sharidan Carrillo
(74) *Attorney, Agent, or Firm*—Brent A. Capehart; Gable & Gotwals

(57) ABSTRACT

A composition and method for cleaning surfaces having deposits, such as drink water tanks, supply water wells, water filter systems, and distributor water lines. The composition contains in combination a cleaning solution and a disinfectant, such as hydrogen peroxide or peracidic acid. The cleaning solution can includes hydrochloric acid and/or phosphoric acid in combination with inhibitors, dyes and water. The composition is applied to deposits which have formed on these surfaces.

3 Claims, No Drawings

COMPOSITION AND METHOD FOR CLEANING SURFACES

REFERENCE TO PENDING APPLICATIONS

This application is a continuation-in-part of United States patent application Ser. No. 09/324,383 filed on Jun. 2, 1999 and entitled A COMPOSITION AND METHOD FOR CLEANING DRINK WATER TANKS.

REFERENCE TO MICROFICHE APPENDIX

This application is not referenced in any microfiche appendix.

BACKGROUND OF THE INVENTION

This invention relates generally to the cleaning of surfaces having deposits and more particularly, to the removal of particular types of deposits formed along these surfaces. Such surfaces are located along internal surfaces of drink water tanks, supply water wells, water filter and distributor water lines.

Typically these surfaces are constantly being exposed to water and air. For example, the water level of a drink water tank rises and falls with demand. This constant change between water exposure and air exposure cause a biological film, such as algae and microorganisms, along with incrustations such as calcium, iron and manganese to form deposits along these surfaces.

Cleaning these deposits from these surfaces has been the subject of a number of prior art compositions. U.S. Pat. No. 4,199,469 issued to Waltzer on Apr. 22, 1980 discloses a composition and method for cleaning drink water tanks. This composition utilizes a group of acids (ascorbic, formic, phosphoric, citric and hydrochloric).

Once the surfaces have been cleaned by a cleaning composition, a disinfectant is normally applied. This additional process adds time and resources to the overall cleaning process. Given the number of constituents the composition is complicated and confusing. Therefore, there exists a need for a more simple composition in order to clean surfaces having deposits contained thereon.

BRIEF SUMMARY OF THE INVENTION

This invention relates generally to the cleaning of surfaces having deposits and more particularly, to the removal of particular types of deposits formed along these surfaces. Such surfaces can be located along internal surfaces of drink water tanks, supply water wells, water filter systems, and distributor water lines.

The present invention is directed, generally, to a composition for such surfaces. The composition includes in combination a cleaning solution portion and a disinfectant portion.

The cleaning solution portion generally includes hydrochloric acid and/or phosphoric acid in combination with inhibitors, dyes and water. The disinfectant is a standard disinfectant, such as but not limited to hydrogen peroxide or peracidic acid.

The composition is applied to the surfaces having deposits of biological film, such as but not limited to algae and microorganisms and/or incrustations such as but not limited to calcium, iron and manganese thereon. The solution loosens the adhesion between the deposits and the surface at which time the composition and deposits are rinsed away. Further, the biological film is reliably eliminated.

It is a primary object of the invention to provide a composition and method for cleaning surfaces that avoids the problems mentioned above.

Another object of the invention is to provide a solution for cleaning and disinfecting such surfaces.

Other objects and further scope of the applicability of the present invention will become apparent from the detailed description to follow wherein like parts are designated by like reference numerals.

DETAILED DESCRIPTION OF THE PREFERRED EMBODIMENTS

This invention relates generally to the cleaning of surfaces having deposits and more particularly, to the removal of particular types of deposits formed along these surfaces. Such surfaces are located along internal surfaces of drink water tanks, supply water wells, water filter systems, and distributor water lines.

The present invention is directed, generally, to a composition for cleaning such surfaces. The composition includes in combination a cleaning solution portion and a disinfectant portion. The composition is applied to drink water tank surfaces have deposits formed thereon.

The cleaning solution portion generally includes hydrochloric acid and/or phosphoric acid in combination with inhibitors, dyes and water. The disinfectant is a standard disinfectant, such as but not limited to hydrogen peroxide or peracidic acid.

The preferred embodiment of the present invention is directed toward the cleaning of surfaces specifically for the removal of deposits which have formed thereon and providing a disinfectant in combination.

With respect to the cleaning solution portion, one basic formula is:

| Ingredients | Weight Percentage (Preferred) |
| --- | --- |
| Sulfamic | 2.0% |
| Citric Acid | 10.0% |
| Glycolic Acid | 14.6% |
| Phosphoric | 12.9% |
| RQDINE ® | 1.8% |
| Hydrochloric Acid | 10.0% |
| Inhibitors | 0.4% |
| Dyes | 0.009% |
| Water | Balance |

| Ingredients | Weight Percentage (Preferred) |
| --- | --- |
| Sulfamic | 2.0% |
| Inhibitors | 0.4% |
| Dyes | 0.009 % |
| Water | Balance |
| Additional formulas include: | |
| Hydrochloric Acid | 9.0% |
| Citric Acid | 0.4% |
| Phosphoric Acid | 2.0% |
| Triethylene glycol | 0.50% |
| Water | Balance |

II

| Ingredients | Weight Percentage (Range) |
| --- | --- |
| Hydrochloric Acid | 5.0–20.0% |
| Phosphoric Acid | 5.0–20.0% |
| Inhibitor | 0.05–1.0% |
| Isopropanol | 0.1–1.0% |
| Water | Balance |

III

| Ingredients | Weight Percentage (Range) |
| --- | --- |
| Phosphoric Acid | 5.0–20.0% |
| Inhibitor | 0.05–1.0% |
| Isopropanol | 0.1–1.0% |
| Water | Balance |

IV

| Ingredients | Weight Percentage (Range) |
| --- | --- |
| Hydrochloric Acid | 5.0–20.0% |
| Inhibitor | 0.05–1.0% |
| Isopropanol | 0.1–1.0% |
| Water | Balance |

V

| Ingredients | Range (Weight Percentage) | |
| --- | --- | --- |
| | Broad | Preferred |
| Amidosulfamic Acid | 4–30% | 10% |
| Nitrilotriacetic Acid | 0.1–0.2% | 0.15% |
| Isopopanol | 0.1–0.5% | 0.3% |
| Water | Balance | Balance |

A disinfectant portion in added to cleaning solution in order to provide a disinfecting capability. The disinfectant portion is a standard disinfectant, such as but not limited to hydrogen peroxide or peracidic acid. The range of the disinfectant portion is 0.1 to 10.0% by volume of the entire composition.

The composition of the preferred embodiment of the present invention is applied to the surface where deposits have formed. These deposits comprise the combination of a biological film, such as algae and microorganisms, with sediments, such as calcium, iron and/or manganese. The composition of the preferred embodiment loosens the adhesive bond between the deposits and the wall surface allowing for the removal thereof. The composition is then rinsed away along with the loosened deposits as well as any remaining biological film.

It is to be understood that the above description is illustrative only and not limiting of the disclosed invention.

The claims and the specification describe the invention presented and the terms that are employed in the claims draw their meaning from the use of such terms in the specification. The same terms employed in the prior art may be broader in meaning than specifically employed herein.

Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. A method of cleaning deposits from a surface selected from the group consisting of drink water tanks, supply water wells, water filter systems, and distributor water lines, said method comprising the steps of:

creating a cleaning composition from a cleaning solution and a disinfectant solution, said cleaning solution consisting of sulfamic acid, citric acid, glycolic acid, phosphoric acid, hydrochloric acid, inhibitors, dyes and water;

applying said cleaning composition to said surface; and rinsing said surface with water in order to remove said deposits from said surface.

2. The method of claim 1 wherein said cleaning corpposition is applied to said surface by pressurized spraying.

3. A method of cleaning deposits from a surface selected from the group consisting of drink water tanks, supply water wells, water filter systems, and distributor water lines, said method comprising the steps of:

creating a cleaning composition from a cleaning solution and a disinfectant solution, said cleaning solution consisting of sulfamic acid, citric acid, glycolic acid, phosphoric acid, hydrochloric acid, inhibitors, dyes and water; and said disinfectant solution selected from the group consisting of hydrogen peroxide and peracidic acid;

applying said cleaning composition to said surface; and rinsing said surface with water in order to remove said deposits from said surface.

* * * * *